United States Patent [19]
Dorsch et al.

[11] Patent Number: 5,389,642
[45] Date of Patent: Feb. 14, 1995

[54] IMIDAZOPYRIDINES

[75] Inventors: Dieter Dorsch, Ober-Ramstadt; Werner Mederski, Erzhausen; Mathias Osswald, Zwingenberg; Pierre Schelling, Mühltal; Norbert Beier, Reinheim; Ingeborg Lues, Darmstadt; Klaus-Otto Minck, Ober-Ramstadt, all of Germany

[73] Assignee: Merck Patent Gesellschaft Mit Beschrankter Haftung, Darmstadt, Germany

[21] Appl. No.: 167,369

[22] Filed: Dec. 16, 1993

[30] Foreign Application Priority Data

Dec. 16, 1992 [DE] Germany .................. 4242459

[51] Int. Cl.$^6$ .................. A61K 31/435; C07D 471/04
[52] U.S. Cl. .................. 514/303; 544/235; 544/238; 544/284; 544/333; 544/362; 546/118
[58] Field of Search .................. 546/118; 514/303

[56] References Cited

U.S. PATENT DOCUMENTS

| | | | |
|---|---|---|---|
| 4,880,804 | 11/1989 | Carini et al. | 514/253 |
| 5,036,048 | 7/1991 | Watkins | 514/16 |
| 5,102,880 | 4/1992 | Chakravarty et al. | 514/212 |
| 5,157,026 | 10/1992 | Chakravarty et al. | 514/81 |
| 5,223,499 | 6/1993 | Greenlee et al. | 514/212 |

FOREIGN PATENT DOCUMENTS

| | | |
|---|---|---|
| 0253310A2 | 1/1988 | European Pat. Off. |
| 0400974A2 | 12/1990 | European Pat. Off. |
| 505893 | 3/1992 | European Pat. Off. |

OTHER PUBLICATIONS

Chiu et al., "Nonpeptide Angiotensin II Receptor Antagonists. III. Structure–Function Studies", *The Journal of Pharmacology and Experimental Therapeutics*, vol. 250, No. 3 (1989), pp. 867–874.

Wong et al., "Nonpeptide Angiotensin II Receptor Antagonists. VIII. Characterization of Functional Antagonism Displayed by DuP 753, an Orally Active Antihypertensive Agent", *Journal of Pharmacology and Experimental Therapeutics*, vol. 252, No. 2 (1990), pp. 719–725.

*Primary Examiner*—Bernard Dentz
*Attorney, Agent, or Firm*—Millen, White, Zelano, & Branigan

[57] ABSTRACT

Novel imidazopyridine derivatives of the formula I

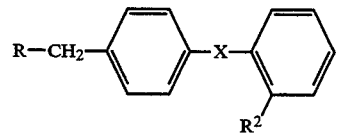

in which
R is

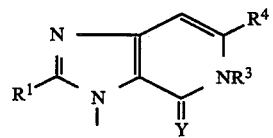

and $R^1$ to $R^4$, X and Y are as defined herein, and their salts have antagonistic properties towards angiotensin-(II) and can be used for the treatment of hypertension, aldosteronism, cardiac insufficiency and increased intraocular pressure and also disorders of the central nervous system.

5 Claims, No Drawings

IMIDAZOPYRIDINES

SUMMARY OF THE INVENTION

The invention relates to novel imidazopyridine derivatives of the formula I:

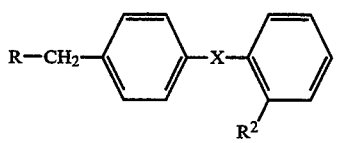

in which

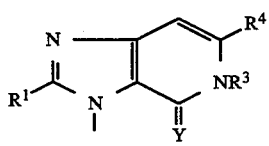

R is Y $R^1$ is $C_3-C_7$-cycloalkyl-$C_nH_{2n}$- or $C_1-C_6$-alkyl, in which a $CH_2$ group is replaced by O or S, $R^2$ is H, $COOR^6$, CN, $NO_2$, $NH_2$, $NHCOR^5$, $NHSO_2R^5$ or 1H-5-tetrazolyl, $R^3$ is —$C_mH_{2m}$—CN, $C_2-C_6$-alkynyl, —$C_mH_{2m}$—Ar, —$C_mH_{2m}$—CO—$R^5$, —$C_mH_{2m}$—CO—AR, —$C_mH_{2m}$—Het or —$C_mH_{2m}$—CO—Het, $R^4$ is H or Hal, $R^5$ is $C_1-C_6$-alkyl, in which one or more H atoms can also be replaced by F, $R^6$ is H or A, X is a single bond or is —NH—CO—, —CO—NH—, —O—CH(COOH)—, —NH—CH(COOH)—, —NA—CH(COOH), —CH=C(COOH), —CH=C(CN) or —CH=C(1H-5-tetrazolyl)—, Y is O or S, A is alkyl having 1–6 C atoms, Ar is an unsubstituted phenyl group or a phenyl group which is monosubstituted or disubstituted by Hal, $R^5$, OH, $OR^5$, $COOR^6$, CN, $NO_2$, $NH_2$, NHA, $N(A)_2$, $NHCOR^5$, NHCOOA, $NHSO_2R^5$ and/or 1H-5- tetrazolyl, Het is a five- or six-membered heteroaromatic radical having 1 to 4N, O and/or S atoms, which can also be fused to a benzene or pyridine ring, Hal is F, Cl, Br or I, m is 1, 2, 3, 4, 5 or 6 and n is 0, 1, 2, 3, 4, 5 or 6, and their salts.

Similar compounds are known from EP-A2-0 400 974 and EP-A1-505 893.

The object of the invention was to find novel compounds with valuable properties, especially those which can be used for the preparation of medicaments.

It was found that the compounds of the formula I and their salts possess very valuable pharmacological properties coupled with a good tolerance. In particular, they have antagonistic properties towards angiotensin II and can therefore be used for the treatment of angiotensin II-dependent hypertension, aldosteronism, cardiac insufficiency and increased intraocular pressure and disorders of the central nervous system, furthermore hypertrophy and hyperplasia of the blood vessels and of the heart, angina pectoris, cardiac infarct, stroke, restenoses after angioplasty or by-pass operations, arteriosclerosis, glaucoma, macular degeneration, hyperuricaemia, kidney function disorders, e.g., kidney failure, diabetic nephropathy, diabetic retinopathy, psoriasis, angiotensin II-mediated disorders in female reproductive organs, perception disorders, e.g., dementia, amnesia, memory function disorders, anxiety states, depression and/or epilepsy.

These effects can be determined by conventional in vitro or in vivo methods such as e.g. those described in U.S. Pat. No. 4,880,804, U.S. Pat. No. 5,036,048 and in WO 91/14367, and also by A. T. Chiu et al., J. Pharmacol. Exp. Therap. 250, 867–874 (1989), and by P. C. Wong et al., ibid. 252, 719–725 (1990; in vivo, on rats).

The compounds of the formula I can be used as pharmaceutical active ingredients in human and veterinary medicine, especially for the prophylaxis and/or therapy of cardiac, circulatory and vascular diseases, in particular of hypertonia cardiac insufficiency and hyperaldosteronism.

The invention relates to the compounds of the formula I and their salts and to a process for the preparation of these compounds and their salts, characterized in that (a) a compound of the formula II

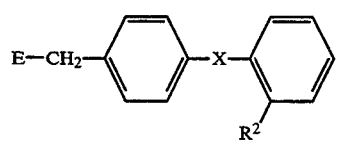

in which

E is Cl, Br, I, a free OH group or an OH group which has been functionally to modified acquire reactivity, and $R^2$ and X are as defined above, is reacted with a compound of the formula III

H-R    III in which

R is as defined above, or (b) a compound of the formula IV

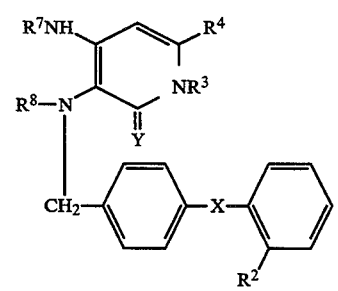

in which $R^7$ is $R^1$—CO or H, $R^8$ is H (if $R^7$ is $R^1$—CO) or $R^1$—CO (if $R^7$ is H) and $R^1$, $R^2$, $R^3$, $R^4$, X and Y are as defined above, is treated with a cyclizing agent, or (c) to prepare a compound of the formula I in which X is —NH—CO— or —CO—NH—, a compound of the formula V

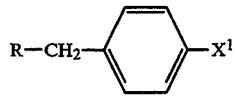

in which $X^1$ is $NH_2$ or COOH and

R is as defined above, or a reactive derivative of this compound is reacted with a compound of the formula VI

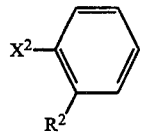

in which $X^2$ is COOH (if $X^1$ is $NH_2$) or $NH_2$ (if $X^1$ is COOH) and $R^2$ is as defined above, or with a reactive derivative of this compound, or (d) a compound of the formula I is set free from one of its functional derivatives by treating with a solvolyzing or hydrogenolyzing agent, or (e) a compound which otherwise corresponds to the formula I, but which instead of the radical $R^3$ contains an H atom, is treated with a compound of the formula E—$R^3$ in which E and $R^3$ are as defined above, and/or in that one or more radicals R and/or $R^2$ in a compound of the formula I are converted to one or more other radicals R and/or $R^2$ and/or a base or acid of the formula I is converted to one of its salts.

Above and below, unless expressly stated otherwise, the radicals or parameters R, $R^1$ to $R^8$, X, Y, A, Ar, Her, Hal, m, n, E, $X^1$ and $X^2$ are as defined in the formulae I to VI.

In the above formulae, A has 1-6, preferably 1, 2, 3 or 4 C atoms. A is preferably methyl, or else ethyl, propyl, isopropyl, butyl, isobutyl, sec-butyl or tert-butyl, or else pentyl, 1-, 2- or 3-methylbutyl, 1,1-, 1,2- or 2,2-dimethylpropyl, 1-ethylpropyl, hexyl, 1-, 2-, 3- or 4-methylpentyl, 1,1-, 1,2-, 1,3-, 2,2-, 2,3- or 3,3-dimethylbutyl, 1- or 2-ethylbutyl, 1-ethyl-1-methylpropyl, 1-ethyl-2-methylpropyl or 1,1,2- or 1,2,2-trimethylpropyl. Alkenyl is preferably vinyl, 1-propenyl or 2-propenyl or 1-butenyl, or else 1-pentenyl or 1-hexenyl. Alkynyl is preferably ethynyl or 1-propynyl or 2-propynyl, or else 1-butynyl, 1-pentynyl or 1-hexynyl.

Hal is preferably F, Cl or Br, or else I.

R is a radical derived from 3H-imidazo[4,5-c]-pyridine ("3H-IP") or, more precisely, 2-$R^1$-4- (thi)oxo-5-$R^3$-6-$R^4$-4,5-dihydro-3H-imidazo[4,5-c]pyridin-3-yl.

Ar is preferably phenyl, o-, m- or p-fluorophenyl, o -, m- or p-chlorophenyl, o -, m- or p-bromophenyl, o-, m- or p-tolyl, o-, m- or p-ethylphenyl, o-, m- or p- trifluoromethylphenyl, o-, m- or p-hydroxyphenyl, o-, m- or p-methoxyphenyl, o-, m- or p-ethoxyphenyl, o-, m- or p-difluoromethoxyphenyl, o-, m- or p-trifluoromethoxyphenyl, o-, m- or p-carboxyphenyl, o-, m- or p-methoxycarbonylphenyl, o-, m- or p-ethoxycarbonylphenyl, o-, m- or p-cyanophenyl, o-, m- or p-nitrophenyl, o-, m- or p-aminophenyl, o-, m- or p-methylaminophenyl, o-, m- or p-dimethylaminophenyl, o-, m- or p-acetamidophenyl, o-, m- or p-trifluoroacetamidophenyl, o-, m- or p-methoxycarbonylaminophenyl, o -, m- or p-ethoxycarbonylaminophenyl, o-, m- or p-methylsulfonamidophenyl, o-, m- or p-trifluoromethylsulfonamidophenyl, o-, m- or p- (1H-tetrazol-5-yl)-phenyl, 2,3-, 2,4-, 2,5-, 2,6-, 3,4- or 3,5-difluorophenyl, 2,3-, 2,4-, 2,5-, 2,6-, 3,4- or 3,5-dichlorophenyl, 2-fluoro-4-nitrophenyl, 2-fluoro- 6-nitrophenyl, 2-chloro-4-nitrophenyl, 2-chloro-6-nitrophenyl, 2-ethoxycarbonyl-4-fluorophenyl, 2-ethoxycarbonyl-6-fluorophenyl, 2-chloro-4-ethoxycarbonylphenyl, 2-chloro-6-ethoxycarbonylphenyl, 2-fluoro-4-methoxycarbonylphenyl, 2-fluoro-6-methoxycarbonylphenyl, 2-chloro-4-methoxycarbonylphenyl or 2-chloro-6-methoxycarbonylphenyl. Of the monosubstituted phenyl groups, those substituted in the o-position are preferred, and of the disubstituted those disubstituted in the 2,6-position are preferred.

Het is preferably 2- or 3-furyl, 2- or -3-thienyl, 1- , 2- or 3-pyrrolyl, 1-, 2-, 4- or 5-imidazolyl, 1-, 3-, 4- or 5-pyrazolyl, 2-, 4- or 5- oxazolyl, 3-, 4- or 5-isoxazolyl, 2-, 4- or 5- thiazolyl, 3-, 4- or 5-isothiazolyl, 1H-1-, 1H-5; 2H-2- or 2H-5-tetrazolyl, 2-, 3- or 4-pyridyl, 2-, 4-, 5- or 6-pyrimidinyl, or else preferably 1,2,3-triazol-1-, -4- or -5-yl, 1,2,4-triazol-1-, -3- or -5-yl, 1,2,3-oxadiazol-4- or -5-yl, 1,2,4-oxadiazol-3- or -5-yl, 1,3,4-thiadiazol-2- or -5-yl, 1,2,4-thiadiazol-3- or -5-yl, 2,1,5-thiadiazol-3- or 4-yl, 3- or 4-pyridazinyl, pyrazinyl, 2-, 3-, 4-, 5-, 6- or -7-benzofuryl, 2-, 3-, 4-, 5-, 6- or 7-benzothienyl, 1-, 2-, 3-, 4-, 5-, 6- or 7-indolyl, 1-, 2-, 3-, 4-, 5-, 6- or 7-isoindolyl, 1-, 2-, 4- or 5-benzimidazolyl, 1-, 3-, 4-, 5-, 6- or 7-benzopyrazolyl, 2-, 4, 5-, 6- or 7-benzoxazolyl, 3-, 4-, 5-, 6- or 7-benzisoxazolyl, 2-, 4-, 5-, 6- or 7-benzothiazolyl, 2-, 4-, 5-, 6- or 7-benzisothiazolyl, 4-, 5-, 6-or 7-benz 2,1,3-oxadiazolyl, 2-, 3-, 4-, 5-, 6-, 7- or 8-quinolyl, 1-, 3-, 4-, 5-, 6-, 7-or 8-isoquinolyl, 3-, 4-, 5-, 6-, 7- or 8-cinnolyl, 2-, 4-, 5-, 6-, 7- or 8-quinazolyl, 1H-1-, -2-, -5-, -6- or -7-imidazo [4,5-b]pyridyl, 3H-2-, -3-, -5-, -6- or -7-imidazo[4,5-b]pyridyl, 3H-1-, -2-, -4-, -6- or -7-imidazo[4,5-c]pyridyl or 3H-2-, -3-, -4-, -6- or -7-imidazo[4,5-c]pyridyl.

The term "Het" also includes the homologous radicals in which the heteroaromatic ring is substituted by one or more, preferably 1 or 2, A groups, preferably methyl and/or ethyl groups, for example 3-, 4- or 5-methyl-2-furyl, 2-, 4- or 5-methyl-3-furyl, 2,4-dimethyl-3-furyl, 3-, 4- or 5-methyl-2-thienyl, 3-methyl-5-tert-butyl-2-thienyl, 2-, 4- or 5-methyl -3-thienyl, 2- or 3-methyl-1-pyrrolyl, 1-, 3-, 4- or 5-methyl-2-pyrrolyl, 3,5-dimethyl-4-ethyl-2-pyrrolyl, 2-, 4- or 5-methyl-1-imidazolyl, 4-methyl-5-pyrazolyl, 4- or 5-methyl-3-isoxazolyl, 3- or 5-methyl-4-isoxazolyl, 3- or 4-methyl-5-isoxazolyl, 3,4-dimethyl-5-isoxazolyl, 4- or 5-methyl-2-thiazolyl, 4- or 5-ethyl-2-thiazolyl, 2- or 5-methyl-4-thiazolyl, 2- or 4-methyl-5-thiazolyl, 2,4-dimethyl-5-thiazolyl, 3-, 4-, 5- or 6-methyl - 2-pyridyl, 2-, 4-, 5- or 6-methyl-3-pyridyl, 2- or 3-methyl-4-pyridyl, 4-methyl-2-pyrimidinyl, 4,5-dimethyl-2-pyrimidinyl, 2-, 5- or 6-methyl -4-pyrimidinyl, 2,6-dimethyl-4-pyrimidinyl, 3, 4-, 5-, 6- or 7-methyl-2 -benzofuryl, 2-ethyl-3 -benzofuryl, 3-, 4-, 5-, 6- or 7-methyl -2-benzothienyl, 3-ethyl-2-benzothienyl, 1-, 2-, 4-, 5-, 6- or 7-methyl-3 indolyl, 1-methyl-5- or -6-benzimidazolyl or 1-ethyl-5-or 6-benzimidazolyl.

The groups —$C_mH_{2m}$— and —$C_nH_{2n}$— are preferably straight-chain and are thus preferably —$CH_2$—, further —$CH_2CH_2$—, —$(CH_2)_3$—, —$(CH_2)_4$—, —$(CH_2)_5$— or —$(CH_2)_6$—, but also e.g. —$CH(CH_3)$—, —$CH_2$—$CH(CH_3)$— or —$C(CH_3)_2$—. The parameter n can preferably also be 0 so that the group —$C_nH_{2n}$— is absent.

The radical $R^1$ is therefore preferably cycloalkyl having 3-7 C atoms, in particular cyclopropyl, further cyclobutyl, cyclopentyl, cyclohexyl, cycloheptyl, furthermore in particular cyclopropylmethyl, 1- or 2-cyclopropylethyl, further cyclobutylmethyl, cyclopentylmethyl, cyclohexylmethyl, methoxy, ethoxy, propoxy, butoxy, isobutoxy, methoxymethyl, ethoxymethyl, propoxymethyl, 2-methoxyethyl, 3-methoxypropyl, 2-ethoxyethyl, methylthio, ethylthio, propylthio, butylthio, isobutylthio, methylthiomethyl, ethylthiomethyl, propylthiomethyl, 2-methylthioethyl, 3-methylthiopropyl or 2-ethylthioethyl.

The radical $R^2$ is preferably 1H-5-tetrazolyl, further preferably COOH, $COOCH_3$, $COOC_2H_5$, CN or $NHSO_2CF_3$.

The radical $R^3$ is preferably —$CH_2CN$, —$CH_2Ar$, —$CH_2$—CO—$R^5$, —$CH_2$—CO—Ar, —$CH_2$—Het or —$CH_2$—CO—Het. In detail, preferred meanings of $R^5$ are cyanoalkyl (in particular cyanomethyl, 2-cyanoethyl, 3-cyanopropyl); alknyl (in particular ethynyl, 1- or 2-propynyl, 1-butyn-1- or -4-yl, 2-butyn-1-yl, 1-pentyn-1- or -5-yl, 2-pentyn-1- or -5-yl); unsubstituted or monosubstituted (preferably in the o-position) or disubstituted (preferably in the 2,6-position) aralkyl, in particular benzyl, 1 - or 2-phenylethyl, 1-, 2 - or 3-phenylpropyl, 1-, 2 -, 3 - or 4phenylbutyl, o-, m- or p - fluorobenzyl, o-, m- or p- chlorobenzyl, o-, m- or p-bromobenzyl, o-, m- or p-methylbenzyl, o-, m- or p-ethylbenzyl, o-, m- or p-trifluoromethylbenzyl, o-, m- or p-hydroxybenzyl, o-, m- or p-methoxybenzyl, o-, m- or p-ethoxybenzyl, o-, m-or p-(difluoromethoxy) benzyl, o-, m- or p-(trifluoromethoxy)benzyl, o-, m- or p-carboxybenzyl, o- , m- or p-methoxycarbonylbenzyl, o-, m- or p-ethoxycarbonylbenzyl, o-, m- or p-cyanobenzyl, o-, m- or p-nitrobenzyl, o-, m- or p-aminobenzyl, o-, m- or p-methylaminobenzyl, o-, m- or p-ethylaminobenzyl, o-, m- or p-isopropylaminobenzyl, o-, m- or p-dimethylaminobenzyl, o-, m- or p-acetamidobenzyl, o-, m- or p-pentanamidobenzyl, o-, m-or p-trifluoroacetamidobenzyl, o-, m- or p-methoxycarbonylaminobenzyl, o-, m- or p-tert-butoxycarbonylaminobenzyl, o-, m- or p-methylsulphonamidobenzyl, o-, m- or p- trifluoromethylsulphonamidobenzyl, o-, m- or p- (1H-5-tetrazolyl)-benzyl, 2,3-, 2,4-, 2,5-, 2,6-, 3,4- or 3,5-difluorobenzyl, 2,3-, 2,4-, 2,5-, 2,6-, 3,4- or 3,5-dichlorobenzyl, 2-chloro-6-fluorobenzyl, 2-chloro-6methylbenzyl, 2-fluoro-6-trifluoromethylbenzyl, 2-chloro-6-trifluoromethylbenzyl, 2-fluoro-6-carboxybenzyl, 2-fluoro-6-methoxycarbonylbenzyl, 2-fluoro-4-nitrobenzyl, 2-fluoro-6-nitrobenzyl, 2-fluoro-6-aminobenzyl, 2-chloro-4-nitrobenzyl, 2-chloro-6-nitrobenzyl, 2-chloro-6-aminobenzyl, 2-ethoxycarbonyl-4-fluorobenzyl, 2-ethoxy-carbonyl-6-fluorobenzyl, 2-chloro-4-ethoxycarbonylbenzyl, 2-chloro-6-ethoxycarbonylbenzyl, 2-fluoro-4-methoxycarbonylbenzyl, 2-fluoro-6-methoxycarbonylbenzyl, 2-chloro-4-methoxycarbonylbenzyl, 2-chloro-6-methoxycarbonylbenzyl, 2,3-, 2,4-, 2,5-, 2,6-, 3,4- or 3,5-dimethoxybenzyl; optionally fluorinated oxoalkyl, in particular 2-oxopropyl, 2-oxobutyl, 3-methyl-2-oxobutyl, 3,3-dimethyl-2-oxobutyl, 3,3,3-trifluoro-2-oxopropyl, 3,3,4,4,4-pentafluoro-2-oxobutyl; unsubstituted or substituted benzoylalkyl, in particular phenacyl (=2-oxo-2-phenylethyl), o-, m- or p-methylphenacyl, o-, m- or p-ethylphenacyl, o-, m- or p-trifluoromethylphenacyl, o-, m- or p-methoxyphenacyl, o-, m- or p-ethoxyphenacyl, o-, m- or p-(difluoromethoxy)phenacyl, o-, m- or p-(trifluoromethoxy)phenacyl, o-, m- or p-carboxyphenacyl, o-, m- or p-methoxycarbonylphenacyl, o-, m- or p-ethoxycarbonylphenacyl, o-, m- or p-cyanophenacyl, o-, m- or p-nitrophenacyl, o-, m- or p-aminophenacyl, o-, m- or p-acetamidophenacyl, o-, m- or p-trifluoroacetamidophenacyl, o-, m- or p-methylsulphonamidophenacyl, o-, m- or p-trifluoromethylsulphonamidophenacyl, o-, m- or p-(1H-5-tetrazolyl)phenacyl; hetalkyl, in particular 2- or 3-furylmethyl, 2- or 3-thienylmethyl, 5-isoxazolylmethyl, 5-methyl-3-isoxazolylmethyl, 2-, 3- or 4-pyridylmethyl, pyrazinylmethyl, 2-, 4-, 5- or 6-pyrimidinylmethyl, 3- or 4-pyridazinylmethyl, 2-, 3-, 4-, 5-, 6- or 7-benzofurylmethyl, 2-, 3- 4-, 5-, 6- or 7-benzothienylmethyl, 2-, 3-, 4-, 5-, 6- or 7-indolylmethyl; Het-CO-alkyl, in particular 2-furoylmethyl, 2-thenoylmethyl, picolinoylmethyl, nicotinoylmethyl, isonicotinoylmethyl, pyrazinecarbonylmethyl, 2-, 4-, 5- or 6-pyrimidinecarbonylmethyl, 3- or 4-pyridazinecarbonylmethyl, benzofuran- 2-, -3-, -4-, -5-, -6- or -7-carbonylmethyl, benzothiophen-2-, -3-, -4-, -5-, -6- or -7- carbonylmethyl or indol - 2-, -3-, -4-, -5-, -6- or -7-carbonylmethyl. Of the substituted phenacyl groups, those substituted in the p-position are preferred.

The radical $R^4$ is preferably H, but also F, Cl, Br or I.

The radical $R^5$ preferably contains 1, 2 or 3 C atoms and is preferably methyl, ethyl, trifluoromethyl, pentafluoroethyl, 2,2,2-trifluoroethyl or 3,3,3-trifluoropropyl. If a compound of the formula I contains two radicals $R^5$, they can be identical to or different from one another.

The radical $R^6$ is preferably H, further preferably methyl or ethyl.

Preferably the radical X is absent or is preferably —NH—CO— or —CO—NH—.

The radical Y is preferably O but also S.

The compounds of the formula I can possess one or more chiral centres and can therefore exist in different forms (optically active or optically inactive). Formula I includes all these forms.

Accordingly, the invention relates especially to those compounds of the formula I in which at least one of the said radicals has one of the preferred meanings indicated above. Some preferred groups of compounds can be expressed by the following partial formulae Ia to Ii, which correspond to the formula I and in which the radicals not described more precisely are as defined in the formula I, in which however:

in Ia X is absent;
in Ib X is —NH—CO—;
in Ic X is —CO—NH—;
in Id X is —O—CH(COOH)—;
in Ie X is —NH—CH(COOH)—;
in If X is —NA—CH(COOH)—;
in Ig X is —CH=C(COOH)—;
in Ih X is —CH=C(CN)—;
in Ii X is —CH=C(1H-5-tetrazolyl)—.

Compounds of the formula Ia are particularly preferred.

The following are additionally preferred:
compounds of the formulae Ik and Iak to Iik, which correspond to the compounds of the formulae I and Ia to Ii, but in which Y is additionally an O atom;
compounds of the formulae Il, Ial to Ikl, and Iakl to Iikl, which correspond to the formulae I, Ia to Ik and Iak to Iik, but in which $R^4$ is additionally H;
compounds of the formulae Im, Iam to Ilm, Ialm to Iklm and Iaklm to Iiklm, which correspond to the formulae I, Ia to Il, Ial to Ikl and Iakl to Iikl, but in which $R^2$ is additionally CN or 1H-5-tetrazolyl.

Among these, those compounds are preferred in which $R^1$ is cyclopropyl.

Further preferred groups of compounds correspond to the formula I and to the other formulae mentioned above, but in which the radical $R^3$ is
(a) $R^5$—CO—CH$_2$—,
(b) Ar—CO—CH$_2$—,
(c) Het—CO—CH$_2$—,
(d) Het—CH$_2$—,
(e) p-aminophenacyl or
(f) o-COOR$^6$-benzyl.

A small selected group of preferred compounds corresponds to the formula I, in which R is a 2-cyclopropyl-4,5-dihydro-4-oxo-5-$R^3$-3H-imidazo [4,5-c]pyridin-3-yl radical,
$R^2$ is 1H-5-tetrazolyl and
$R^3$ is o-methoxycarbonylbenzyl or o-ethoxycarbonylbenzyl
and
X is absent, i.e., a single bond.

The compounds of the formula I and also the starting materials for their preparation are moreover prepared by methods known per se, such as those described in the literature (e.g. in the standard works such as Houben-Weyl, Methoden der organischen Chemie (Methods of Organic Chemistry), Georg-Thieme-Verlag, Stuttgart, but especially in EP-A2-0 430 709 and in U.S. Pat. No. 4,880,804), under reaction conditions which are known and suitable for said reactions, it also being possible to make use of variants known per se, which are not mentioned in greater detail here.

If desired, the starting materials can also be formed in situ, so that they are not isolated from the reaction mixture but immediately reacted further to give the compounds of the formula I.

The compounds of the formula I can preferably be obtained by reacting compounds of the formula II with compounds of the formula III. Particularly the biphenyl derivatives of the formula I (in which X is absent) are readily obtainable in this way.

In the compounds of the formula II, E is preferably Cl, Br, I or an OH group which has been functionally modified to acquire reactivity, such as alkylsulphonyloxy having 1-6 C atoms (preferably methylsulphonyloxy) or arylsulphonyloxy having 6-10 C atoms (preferably phenyl-or p-tolylsulphonyloxy).

The reaction of II with III is expediently carried out by first converting III to a salt by treatment with a base, e.g. with an alkali metal alcoholate such as CH$_3$ONa or K tert-butylate in an alcohol such as CH$_3$OH, or with an alkali metal hydride such as NaH or with an alkali metal alcoholate in dimethylformamide (DMF), and then reacting said salt with II in an inert solvent, e.g. an amide such as DMF, N-methylpyrrolidinone or dimethylacetamide, or a sulphoxide such as dimethyl sulphoxide (DMSO), expediently at temperatures of between −20°0 and 100°, preferably of between 10° and 30°. Other suitable bases are alkali metal carbonates such as Na$_2$CO$_3$ or K$_2$CO$_3$, or alkali metal hydrogen carbonates such as NaHCO$_3$ or KHCO$_3$.

The compounds of the formula I can also be obtained by the cyclization of compounds of the formula IV. This cyclization is expediently carried out by heating with polyphosphoric acid, acetic acid or diglyme to temperatures of between about 80° and 180°, preferably of between 120° and 160°.

Acid amides of the formula I (X=—NH—CO— or —CO—NH—) can also be obtained by reacting compounds of the formula V (or reactive derivatives thereof) with compounds of the formula VI (or reactive derivatives thereof).

Suitable reactive derivatives of the carboxylic acids of the formulae V and VI ($X^1$ or $X^2$=COOH) are advantageously the corresponding chlorides, bromides or anhydrides. The reaction is expediently carried out in the presence of an inert solvent, e.g., a halogenated hydrocarbon such as dichloromethane, chloroform, trichloroethene or 1,2-dichloroethane, or an ether such as tetrahydrofuran (THF) or dioxane, at temperatures of between 0° and 150°, preferably of between 20° and 80°. If acid halides are reacted, it is recommended to add a base, e.g., a tertiary amine such as triethylamine, pyridine or 4-dimethylaminopyridine.

A compound of the formula I can also be set free from one of its functional derivatives by treating with a solvolyzing (e.g., hydrolyzing) or hydrogenolyzing agent.

It is thus possible according to one of the methods given to prepare a compound which corresponds to the formula I, but instead of a 5-tetrazolyl group contains a 1H- or 2H- 5- tetrazolyl group functionally modified (protected by a protective group) in the 1- or 2-position. Suitable protective groups are, for example: triphenylmethyl, which can be removed with HCl or formic acid in an inert solvent or solvent mixture, e.g., ether/dichloromethane/methanol; 2-cyanoethyl, which can be removed with NaOH in water/THF; p-nitrobenzyl, which can be removed with H$_2$/Raney nickel in ethanol.

Carboxylic acids of the formula I in which X is —O—CH(COOH), —NH—CH(COOH), —NA—CH(COOH) or —CH=C(COOH) can also be obtained by hydrolysis of corresponding alkyl esters, e.g., with NaOH or KOH in aqueous solution with or without addition of an inert organic solvent such as methanol, ethanol, THF or dioxane, at temperatures of between 0° and 100°, or by hydrogenolysis of corresponding benzyl esters, e.g., on Pd on carbon at pressures of between 1 and 200 bar and at temperatures of between 0° and 100° in one of the inert solvents given.

Furthermore, a compound otherwise corresponding to the formula I, but which contains an H atom instead of the radical $R^3$, can be treated with a compound of the formula E-$R^3$.

Typical compounds of the formula E-$R^3$ are, e.g., chloro- or bromoacetonitrile, propargyl chloride or bromide, benzyl chloride or bromide, methyl or ethyl o-chloromethyl- or o-bromomethylbenzoayes, chloro- or bromoacetone, phenacyl chloride or bromide, 2-thienylmethyl chloride or bromide, 2-furoylmethyl chloride or bromide.

This reaction is preferably carried out in an acid amide such as DMF, N-methylpyrrolidone, 1,3-dimethyl-2-oxohexahydropyrimidine or hexamethylphosphoramide, an alcohol such as methanol or tert-butanol, an ether such as THF, or a halogenated hydrocarbon such as dichloromethane, or mixtures thereof, as the solvent, and/or in the presence of an alkali metal alcoholate such as sodium methylate or potassium tert-butylate, an alkali metal hydride such as sodium or potassium hydride, an alkali metal carbonate such as sodium or potassium carbonate, an alkali metal bicarbonate such as sodium or potassium bicarbonate, or a tertiary amine such as triethylamine or ethyldiisopropylamine, at temperatures of between about −30 and 200, preferably of between 20° and 60°.

Some of the starting materials, especially those of the formula II, are known. If they are not known, they can be prepared by known methods analogously to known substances. Compounds of the formula III ($R^4$=H, Y=O) can be obtained, e.g., by reacting carboxylic acids of the formula $R^1$—COOH with compounds of the formula VII

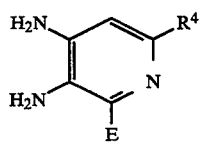

VII in the presence of polyphosphoric acid, the group E (preferably Cl) being hydrolyzed in the process, and compounds corresponding to III initially resulting, but in which there is an H atom instead of $R^3$; these are then reacted with compounds of the formula E-$R^3$.

Compounds of the formula V can be obtained, e.g., by reacting compounds of the formula VIII

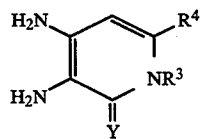

VIII in which, however, one of the amino groups is protected by an amino-protective group (e.g., benzyl, A—O—CO— or benzyloxycarbonyl), with compounds of the formula II and subsequently removing the protective group and reacting the products with acids of the formula $R^1$—COOH or functional derivatives thereof; they are not normally isolated, but are formed in situ in the last-mentioned reaction.

It is also possible to convert a compound of the formula I to another compound of the formula I by converting one or more of the radicals R and/or $R^2$ to other radicals R and/or $R^2$, e.g., by reducing nitro groups to amino groups (e.g., by hydrogenation on Raney nickel or Pd carbon in an inert solvent such as methanol or ethanol), and/or functionally modifying free amino and/or hydroxyl groups, and/or freeing functionally modified amino and/or hydroxyl groups by solvolysis or hydrogenolysis, and/or hydrolyzing nitrile groups to COOH groups, or converting nitrile groups to tetrazolyl groups with hydrazoic acid derivatives, e.g., sodium azide in N-methylpyrrolidone or trimethyltin azide in toluene.

Thus, for example, free amino groups can be acylated in a conventional manner with an acid chloride or anhydride, or alkylated with a substituted or unsubstituted alkyl halide, expediently in an inert solvent such as dichloromethane or THF, and/or in the presence of a base such as triethylamine or pyridine, at temperatures of between −60° and +30°.

If desired, a functionally modified amino and/or hydroxyl group in a compound of the formula I can be freed by solvolysis or hydrogenolysis using conventional methods. Thus, e.g., a compound of the formula I containing an NHCOR$^5$ or a COOA group can be converted to the corresponding compound of the formula I containing an NH$_2$ or a COOH group instead. COOA groups can be saponified, e.g., with NaOH or KOH in water, water/TF or water/dioxane, at temperatures of between 0° and 100°.

The reaction of nitriles of the formula I (e.g., those where $R^2$=CN) with hydrazoic acid derivatives leads to tetrazoles of the formula I (e.g., where $R^2$=1H-5-tetrazolyl). It is preferable to use trialkyltin azides such as trimethyltin azide, in an inert solvent, e.g., an aromatic hydrocarbon such as toluene, at temperatures of between 20° and 150°, preferably of between 80° and 140°, or sodium azide in N-methylpyrrolidone at temperatures of between about 100° and 200°.

A base of the formula I can be converted with an acid to the corresponding acid addition salt. Suitable acids for this reaction are especially those which yield physiologically acceptable salts. Thus it is possible to use inorganic acids, e.g., sulphuric acid, nitric acid, hydrohalic acids such as hydrochloric acid or hydrobromic acid, phosphoric acids such as orthophosphoric acid, and sulphamic acid, as well as organic acids, especially aliphatic, alicyclic, araliphatic, aromatic or heterocyclic monobasic or polybasic carboxylic, sulphonic or sulphuric acids, e.g., formic acid, acetic acid, propionic acid, pivalic acid, diethylacetic acid, malonic acid, succinic acid, pimelic acid, fumaric acid, maleic acid, lactic acid, tartaric acid, malic acid, citric acid, gluconic acid, astorbit acid, nicotinic acid, isonicotinic acid, methane- or ethanesulphonic acid, ethanedisulphonic acid, 2-hydroxyethanesulphonic acid, benzenesulphonic acid, p-toluenesulphonic acid, naphthalenemonosulphonic and -disulphonic acids and laurylsulphuric acid. Salts with physiologically unacceptable acids, e.g., picrates, can be used for isolating and/or purifying the compounds of the formula I.

On the other hand, compounds of the formula I containing COOH or tetrazolyl groups can be converted with bases (e.g., sodium or potassium hydroxide or carbonate) to the corresponding metal salts, especially alkali metal or alkaline earth metal salts, or to the corresponding ammonium salts. The potassium salts of the tetrazolyl derivatives are particularly preferred.

The novel compounds of the formula I and their physiologically acceptable salts can be used for the manufacture of pharmaceutical preparations by incorporation into a suitable dosage form together with at least one excipient or auxiliary and, if desired, together with one or more other active ingredient(s). The resulting formulations can be used as medicaments in human or veterinary medicine. Possible excipients are organic or inorganic substances which are suitable for enteral (e.g., oral or rectal) or parenteral administration or for administration in the form of an inhalation spray, and which do not react with the novel compounds, for example water, vegetable oils, benzyl alcohols, polyethylene glycols, glycerol triacetate and other fatty acid glycerides, gelatin, soya lecithin, carbohydrates such as lactose or starch, magnesium stearate, talc and cellulose. Tablets, coated tablets, capsules, syrups, juices or drops, in particular, are used for oral administration; lacquered tablets and capsules with coatings or shells resistant to gastric juices are of special interest. Suppositories are used for rectal administration and solutions, preferably oily or aqueous solutions, as well as suspensions, emulsions or implants, are used for parenteral administration. For administration as inhalation sprays, it is possible to use sprays containing the active ingredient either dissolved or suspended in a propellant mixture (e.g., hydrochlorofluorocarbons). It is expedient here to use the active ingredient in micronized form, it being possible for one or more additional physiologically compatible solvents, e.g. ethanol, to be present. Inhalation solutions can be administered with the aid of conventional inhalers. The novel compounds can also be lyophilizedand the resulting lyophilizates used, e.g., for the manufacture of injection preparations. The indicated formulations can be sterilized and/or can contain auxiliaries such as preservatives, stabilizers and/or wetting agents, emulsifiers, salts for influencing the osmotic pressure, buffer substances, colours and/or flavourings. If desired, they can also contain one or more other active ingredients, e.g., one or more vitamins, diuretics or antiphlogistics.

The substances according to the invention are normally administered analogously to other known, commercially available preparations, but in particular analogously to the compounds described in U.S. Pat. No. 4,880,804, preferably in dosages of between about 1 mg and 1 g, especially of between 50 and 500 mg per dosage unit. The daily dosage is preferably between about 0.1 and 50 mg/kg, especially between 1 and 10 mg/kg of body weight. However, the special dose for each particular patient depends on a very wide variety of factors, for example on the efficacy of the special compound used, age, body weight, general state of health, sex, diet, time and method of administration, rate of excretion, medicament combination and severity of the particular disease to which the therapy is applied. Oral administration is preferred.

Above and below, all temperatures are given in °C. In the following Examples, "conventional working-up" means: water is added if necessary, the pH is adjusted to between 2 and 10 if necessary, depending on the constitution of the end product, extraction is carried out with ethyl acetate or dichloromethane and the organic phase is separated off, dried over sodium sulphate, evaporated and purified by chromatography on silica gel and/or by crystallization. IP=imidazo[4,5-C]pyridine $R_f$ values on silica gel (by thin-layer chromatography), FAB=- mass spectrum, obtained by the fast atom bombardment method, (M+H)+ peak.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosures of all applications, patents and publications, cited above and below, and of corresponding application German P 42 42 459.3, filed Dec. 16, 1992, are hereby incorporated by reference.

EXAMPLES

Example 1

(a) A solution of 0.23 g of Na in 20 ml of methanol is added dropwise in the course of 15 minutes to a solution of 2.55 g of 2-cyclopropyl-5-(2-furyl-methyl)-4,5-dihydro-4-oxo-3H-IP [obtainable by condensation of cyclopropanecarboxylic acid with 3,4-diamino-2-chloropyridine in the presence of polyphosphoric acid to give 2-cyclopropyl-4,5-dihydro-4-oxo-1 (or 3) H-IP, reaction with benzyl bromide in methanol in the presence of CH$_3$ONa to give 3-benzyl-2-cyclopropyl-4,5-dihydro-4-oxo-3H-IP, reaction with 2-furylmethyl chloride in DMF in the presence of K tert-butylate to give 3-benzyl-2-cyclopropyl-5-(2-furylmethyl)-4,5-dihydro-4-oxo-3H-IP and hydrogenolytic cleavage of the benzyl group] in 75 ml of methanol. The mixture is stirred at 20° for a further 30 minutes, evaporated, the residue is dissolved in 20 ml of DMF and a solution of 3.05 g of methyl 4'-bromomethylbiphenyl-2-carboxylate (IIa) in 10 ml of DMF is added dropwise at 0° with stirring. The mixture is stirred at 20° for 16 hours, evaporated, worked up in the conventional manner and chromatographed on silica gel to give 2-cyclopropyl-5-(2-furylimethyl)-4,5-dihydro-3-(2'-methoxycarbonylbiphenylyl-4-methyl)-4-oxo-3H-IP.

(b) A mixture of 1 g of the methyl ester obtained as in (a), 12 ml of aqueous 2 N NaOH solution and 48 ml of methanol is boiled for 2 hours and then evaporated. The mixture is worked up in the conventional manner (aqueous hydrochloric acid to pH 3/dichloromethane) and gives 2-cyclopropyl-5-(2-furylmethyl)-4,5-dihydro-3-(2'-carboxybiphenylyl-4-methyl)-4-oxo-3H-IP.

Example 2

Analogously to Example 1, 2-cyclopropyl-5-(o-ethoxycarbonylbenzyl)-3-[p-(2-cyano-2-phenylvinyl)-benzyl]-4,5-dihydro-4-oxo-3H-IP is obtained from 3.37 g of 2-cyclopropyl-5-(o-ethoxycarbonylbenzyl)-4,5-dihydro-4-oxo-3H-IP and 2.98 g of 3-p-bromomethylphenyl-2-phenylacrylonitrile [m.p. 178°; obtainable by condensation of p-tolylaldehyde with phenylacetonitrile in the presence of C$_2$H$_5$ONa in ethanol to give 2-phenyl-3-p-tolylacrylonitrile (m.p. 61°) and bromination with N-bromosuccinimide in dichloromethane].

Example 3

A mixture of 0.86 g of cyclopropanecarboxylic acid, 4.55 g of 4-amino-1,2-dihydro-2-oxo-3-[2'-(1H-5tetrazolyl) biphenylyl-4-methylamino]-1-(o-ethoxycarbonylbenzyl)-pyridine [obtainable by reaction of 3-amino-4-benzylamino-1,2-dihydro-2-oxo-1-(o-ethoxycarbonylbenzyl)pyridine with 4-bromomethyl-2'-cyanobiphenyl to give 4-benzylamino-3-(2'-cyanobiphenylyl-4-methylamino)-1,2-dihydro-2-oxo-1-(o-ethoxycarbonylbenzyl)pyridine, reaction with trimethyltin azide to give 4-benzylamino-1,2dihydro-2-oxo-3-[2'-(1H-5-tetrazolyl)biphenylyl-4-methyl-amino]-1-(o-ethoxycarbonylbenzyl)pyridine and hydrogenolytic cleavage of the benzyl group] and 50 g of polyphosphoric acid is heated at 140° for 5 hours. Intermediates formed in situ are 4-amino-1,2-dihydro-2-oxo-3-[2'-(1H-5-tetrazolyl)-biphenylyl]-4-methyl-N-cyclopropylcarbonylamino]-1-(o-ethoxycarbonylbenzyl)pyridine and 1,2-dihydro-2-oxo-3-[2'-(1H-5-tetrazolyl)biphenylyl-4-methylamino]-1-(o-ethoxycarbonylbenzyl)-4-cyclopropylcarbonylaminopyridine. The mixture is cooled, poured onto ice, rendered alkaline using sodium hydroxide solution, and worked up in the conventional manner to give 2-cyclopropyl-4,5-dihydro-5-(o-ethoxycarbonyl-benzyl)-4-oxo-3-[2'-(1H-5-tetrazolyl)biphenylyl-4-methyl]-3H-IP.

Example 4

A mixture of 1.1 g of 3-p-aminobenzyl-2-cyclo-propyl-4,5-dihydro-4-oxo-5-(2-thienylmethyl)-3H-IP [obtainable by reaction of 2-cyclopropyl-4,5-dihydro-4-oxo-5-(2-thienylmethyl)-3H-IP with p-nitrobenzyl bromide to give 2-cyclopropyl-4,5-dihydro-3-p-nitro-benzyl-4-oxo-5-(2-thienylmethyl)-3H-IP and subsequent hydrogenation], 0.6 g of phthalic anhydride and 40 ml of $CHCl_3$ is stirred at 20° for 16 hours. The precipitated 2-cyclopropyl-3-[4-(o-carboxybenzamido)benzyl]-4,5-dihydro-4-oxo-5- (2-thienylmethyl) -3H-IP is filtered off.

Example 5

A mixture of 3.76 g of 3-p-aminobenzyl-2-cyclo-propyl-4,5-dihydro-4-oxo-5-(2-thienylmethyl)-3H-IP, 3 ml of triethylamine, 0.5 g of 4-dimethylaminopyridine and 120 ml of dichloromethane is cooled to 5° and treated dropwise with a solution of 2.88 g of o-trifluorome-thane-sulphonamidobenzoyl chloride in 20 ml of dichloromethane. The mixture is stirred at 20° for a further 16 hours, evaporated and worked up in the conventional manner and gives 2-cyclopropyl-4,5-dihydro-4-oxo-5-(2-thienylmethyl)-3-[4-(o-trifluoromethanesul-phonamidobenzamido)benzyl]-3H-IP.

Example 6

A mixture of 4.72 g of 2-cyclopropyl-3-p-carboxy-benzyl-4,5-dihydro-5-p-nitrophenacyl-4-oxo-3H-IP, 12 g of thionyl chloride and 35 ml of $CHCl_3$ is boiled for 6 hours and evaporated. The red acid chloride obtained is freed from thionyl chloride residues by dissolving in toluene and evaporating several times, and is dissolved in 80 ml of THF. This solution is added dropwise to a solution of 1.7 g of anthranilic acid and 0.8 g of NaOH in 100 ml of water, stirred for 24 hours and acidified to pH 5 using hydrochloric acid. Conventional working-up gives 2-cyclopropyl-3-[p-(2-carboxyanilinocar-bonyl)benzyl]-4,5-dihydro-5-p-nitrophenacyl-4-oxo-3H-IP.

Example 7

(a) A solution of 2.94 g of 2-cyclopropyl-3-(2'-cyanobiphenylyl-4-methyl)-4,5-dihydro-4-oxo-3H-IP (m.p. 183°; obtainable by reaction of 3,4-diamino-2-chloropyridine with cyclopropane-carboxylic acid analogously to Example 3 (reaction time 18 hours) to give 2-cyclopropyl-4,5-dihydro-4-oxo-1 (or 3) H-IP ($R_f$ 0.27 in ethyl acetate/methanol 8:2; FAB 176) and reaction with 4'-bromomethyl-2-cyanobiphenyl in N-methylpyrrolidinone in the presence of $K_2CO_3$) in 60 ml of N-methylpyrrolidinone is treated with 1.25 g of K tert-butylate while stirring at 20°. After stirring for 45 minutes, a solution of 4.6 g of methyl o-bromomethyl-benzoate in 25 ml of DMF is added dropwise. The mixture is stirred at 20° for a further 16 hours, worked up in the conventional manner and gives 2-cyclopropyl-3-(2'-cyano-biphenylyl-4-methyl)-4,5-dihydro-5-(o-methoxycarbonylbenzyl)-4-oxo-3H-IP; $R_f$ 0.41 (petroleum ether/ethyl acetate 2:8); FAB 515.

The 2-cyclopropyl-3-(2'-cyanobiphenylyl-4-methyl)-4,5-dihydro-4-oxo-5-$R^3$-3H-IP below are obtained analogously:

| | |
|---|---|
| with chloroacetonitrile: | -5-cyanomethyl- |
| with 3-bromopropionitrile: | -5-(2-cyanoethyl)- |
| with 4-bromobutyronitrile: | -5-(3-cyanopropyl)- |
| with propargyl bromide: | -5-propargyl- |
| with benzyl bromide: | -5-benzyl- |
| with o-fluorobenzyl bromide: | -5-(o-fluorobenzyl)- |
| with m-fluorobenzyl bromide: | -5-(m-fluorobenzyl)- |
| with p-fluorobenzyl bromide: | -5-(p-fluorobenzyl)- |
| with o-chlorobenzyl bromide: | -5-(o-chlorobenzyl)-, $R_f$ 0.48 (petroleum ether/ethyl acetate 2:8) |
| with m-chlorobenzyl bromide: | -5-(m-chlorobenzyl)- |
| with p-chlorobenzyl bromide: | -5-(p-chlorobenzyl)- |
| with o-bromobenzyl bromide: | -5-(o-bromobenzyl)- |
| with m-bromobenzyl bromide: | -5-(m-bromobenzyl)- |
| with p-bromobenzyl bromide: | -5-(p-bromobenzyl)- |
| with p-methylbenzyl bromide: | -5-(p-methylbenzyl)- |
| with o-trifluoromethyl-benzyl bromide: | -5-(o-trifluoromethyl-benzyl)- |
| with m-trifluoromethylbenzyl bromide: | -5-(m-trifluoromethyl-benzyl)- |
| with p-trifluoromethylbenzyl bromide: | -5-(p-trifluoromethyl-benzyl)- |
| with m-methoxycarbonylbenzyl bromide: | -5-(m-methoxycarbonyl-benzyl)- |
| with p-methoxycarbonylbenzyl bromide: | -5-(p-methoxycarbonyl-benzyl)- |
| with o-ethoxycarbonylbenzyl bromide: | -5-(o-ethoxycarbonyl-benzyl)-, Rf 0.7 (ethyl acetate) |
| with m-ethoxycarbonylbenzyl bromide: | -5-(methoxycarbonyl-benzyl)- |
| with p-ethoxycarbonylbenzyl bromide: | -5-(p-ethoxycarbonyl-benzyl)- |
| with o-cyanobenzyl bromide: | -5-(o-cyanobenzyl)- |
| with m-cyanobenzyl bromide: | -5-(m-cyanobenzyl)- |
| with p-cyanobenzyl bromide: | -5-(p-cyanobenzyl)- |
| with o-nitrobenzyl chloride: | -5-(o-nitrobenzyl)- |
| with m-nitrobenzyl chloride: | -5-(m-nitrobenzyl)- |
| with p-nitrobenzyl chloride: | -5-(p-nitrobenzyl)- |
| with o-trifluoroacet-amidobenzyl bromide: | -5-(o-trifluoroacetamido-benzyl)- |
| with m-trifluoroacet-amidobenzyl bromide: | -5-(m-trifluoroacetamido-benzyl)- |
| with p-trifluoroacet-amidobenzyl bromide: | -5-(p-trifluoroacetamido-benzyl)- |
| with o-trifluoromethylsul-phonamidobenzyl bromide: | -5-(o-trifluoromethyl-sulphonamidobenzyl)- |
| with m-trifluoromethylsul-phonamidobenzyl bromide: | -5-(m-trifluoromethyl-sulphonamidobenzyl)- |
| with p-trifluoromethylsul-phonamidobenzyl bromide: | -5-(p-trifluoromethyl-sulphonamidobenzyl)- |
| with 2,6-dichlorobenzyl bromide: | -5-(2,6-dichlorobenzyl)- |
| with 2-fluoro-6-nitrobenzyl bromide: | -5-(2-fluoro-6-nitro-benzyl)- |
| with 2-chloro-6-nitrobenzyl bromide: | -5-(2-chloro-6-nitro-benzyl)- |
| with 2-furylmethyl chloride: | -5-(2-furylmethyl)- |
| with 2-thienylmethyl chloride: | -5-(2-thienylmethyl)- |
| with 5-isoxazolylmethyl bromide: | -5-(5-isoxazolylmethyl)- |
| with 5-methyl-3-isoxazolyl-methyl bromide: | -5-(5-methyl-3-isoxazo-lylmethyl)- |
| with 2-pyridylmethyl chloride: | -5-(2-pyridylmethyl)- |
| with 4-pyridylmethyl chloride: | -5-(4-pyridylmethyl)- |

| | |
|---|---|
| with 2-(2-furyl)-2-oxo-ethyl bromide: | -5-(2-furoylmethyl)- |
| with 2-(2-thienyl)-2-oxo-ethyl bromide: | -5-(2-thenoylmethyl)- |
| with bromo- or chloro-acetone: | -5-(2-oxopropyl)- |
| with phenacyl chloride or bromide: | -5-phenacyl- |
| with o-methoxyphenacyl chloride: | -5-o-methoxyphenacyl- |
| with 1-bromo-2-butanone: | -5-(2-oxobutyl)- |
| with 1-bromo-3-methyl-2-butanone: | -5-(3-methyl-2-oxobutyl)- |
| with 1-bromo-3,3-dimethyl-2-butanone: | -5-(3,3-dimethyl-2-oxobutyl)-, Rf 0.71 (ethyl acetate/methanol 9:1) |
| with o-nitrophenacyl chloride: | -5-o-nitrophenacyl- |
| with m-nitrophenacyl chloride: | -5-m-nitrophenacyl- |
| with p-nitrophenacyl chloride: | -5-p-nitrophenacyl- |
| with 1-bromo-3,3,3-trifluoroacetone: | -5-(3,3,3-trifluoro-2-oxopropyl)- |
| with 1-bromo-3,3,4,4,4-pentafluoro-2-butanone: | -5-(3,3,4,4,4-pentafluoro-2-oxobutyl)- |
| with 2-(3-pyridyl)-2-oxo-ethyl chloride: | -5-nicotinoylmethyl- |
| with p-difluoromethoxyphenacyl chloride: | -5-p-difluoromethoxyphenacyl- |
| with p-trifluoromethoxyphenacyl chloride: | -5-p-trifluoromethoxyphenacyl- |
| with p-cyanophenacyl chloride: | -5-p-cyanophenacyl- |
| with 2-(2-benzofuryl)-2-oxoethyl bromide: | -5-[2-(2-benzofuryl)-2-oxoethyl]-. |

(b) A mixture of 3.9 g of the compound obtained as in (a), 5 g of trimethyltin azide and 100 ml of toluene is boiled for 72 hours and then evaporated. The residue is taken up in 100 ml of methanolic HCl, stirred at 20° for 2 hours and worked up in the conventional manner (saturated NaCl solution/dichloromethane) . Chromatography (ethyl acetate/methanol 9:1) yields 2-cyclopropyl-4,5-dihydro-5-(o-methoxycarbonylbenzyl)-4-oxo-3-[2'-(1H-5-tetrazolyl)biphenylyl-4-methyl]-3H-IP, m.p. 260°.

The 2-cyclopropyl-4,5-dihydro-4-oxo-3-[2'-(1H-5-tetrazolyl)biphenylyl- 4-methyl]-5-R$^3$-3H-IP below are obtained analogously from the 2'- cyanobiphenylyl compounds given in (a):
-5-propargyl-
-5-benzyl-
-5-(o-fluorobenzyl)-
-5-(m-fluorobenzyl)-
-5-(p-fluorobenzyl)-
-5-(o-chlorobenzyl)-, m.p. 185°
-5-(m-chlorobenzyl)-
-5-(p-chlorobenzyl)-
-5-(o-bromobenzyl)-
-5-(m-bromobenzyl)-
-5-(p-bromobenzyl)-
-5-(p-methylbenzyl)-
-5-(o-trifluoromethylbenzyl)-
-5-(m-trifluoromethylbenzyl)-
-5-(p-trifluoromethylbenzyl)-
-5-(m-methoxycarbonylbenzyl)-
-5-(p-methoxycarbonylbenzyl)
-5-(o-ethoxycarbonylbenzyl)-, K salt , m.p. >300°
-5-(m-ethoxycarbonylbenzyl)-
-5-(p-ethoxycarbonylbenzyl)-
-5-[o-(1H-5-tetrazolyl)benzyl]-
-5-[m-(1H-5-tetrazolyl)benzyl]-
-5-[p-(1H-5 -tetrazolyl)benzyl]-
-5-(o-nitrobenzyl)-
-5-(m-nitrobenzyl)-
-5-(p-nitrobenzyl)-
-5-(o-trifluoroacetamidobenzyl)-
-5-(m-trifluoroacetamidobenzyl)-
-5-(p-trifluoroacetamidobenzyl)-
-5-(o-trifluoromethylsulphonamidobenzyl)-
-5-(m-trifluoromethylsulphonamidobenzyl)-
-5-(p-trifluoromethylsulphonamidobenzyl)-
-5-(2-fluoro-6-nitrobenzyl)-
-5-(2-chloro-6-nitrobenzyl)-
-5-(2-furylmethyl)-
-5-(2-thienylmethyl)-
-5-(5-isoxazolylmethyl)-
-5-(5-methyl-3-isoxazolylmethyl)-
-5-(2-pyridylmethyl)-
-5-(3-pyridylmethyl)-
-5-(4-pyridylmethyl)-
-5-(2-furoylmethyl)-
-5-(2-thenoylmethyl)-
-5-(2-oxopropyl)-
-5-phenacyl-
-5-o-methoxyphenacyl-
-5-(2-oxobutyl)-
-5-(3-methyl-2-oxobutyl)-
-5-(3,3-dimethyl-2-oxobutyl)-, m.p.153°
-5-o-nitrophenacyl-
-5-m-nitrophenacyl-
-5-p-nitrophenacyl-
-5-(3,3,3-trifluoro-2-oxopropyl)-
-5-(3,3,4,4,4-pentafluoro-2-oxobutyl)-
-5-nicotinoylmethyl-
-5-p-difluoromethoxyphenacyl-
-5-p-trifluoromethoxyphenacyl-
-5-p-cyanophenacyl-
-5-[2-(2-benzofuryl)-2-oxoethyl]-.

Example 8

(a) Analogously to Example 7, 2-cyclopropyl-4,5-dihydro-5-(o-ethoxycarbonylbenzyl)-4-oxo-3-[2'-(2-triphenyl-methyl-2H-tetrazolyl)biphenylyl-4-methyl]-3H-IP is obtained from 2-cyclopropyl-4,5-dihydro-4-oxo-3-[2'-(2-triphenylmethyl-2H-5-tetrazolyl)biphenylyl-4-methyl]-3H-IP with ethyl o-bromomethylbenzoate.

The 2-cyclopropyl-4,5-dihydro-4-oxo-3-[2'-(2-triphenylmethyl-2H-5-tetrazolyl)biphenylyl-4-methyl]-5-R$^3$-3H-IP below are obtained analogously:

-5-propargyl-
-5-benzyl-
-5-(o-fluorobenzyl)-
-5-(m-fluorobenzyl)-
-5-(p-fluorobenzyl)-
-5-(o-chlorobenzyl)-
-5-(m-chlorobenzyl)-
-5-(p-chlorobenzyl)-
-5-(o-bromobenzyl)-
-5-(m-bromobenzyl)-
-5-(p-bromobenzyl)-
-5-(p-methylbenzyl)-
-5-(o-trifluoromethylbenzyl)-
-5-(m-trifluoromethylbenzyl)-
-5-(p-trifluoromethylbenzyl)-
-5-(o-methoxycarbonylbenzyl)-
-5-(m-methoxycarbonylbenzyl)-

-5-(p-methoxycarbonylbenzyl)-
-5-(m-ethoxycarbonylbenzyl)-
-5-(p-ethoxycarbonylbenzyl)-
-5-[o-(1H-5-tetrazolyl)benzyl]-
-5-[m-(1H-5-tetrazolyl)benzyl]-
-5-[p-(1H-5-tetrazolyl)benzyl]-
-5-(o-nitrobenzyl)-
-5-(m-nitrobenzyl)-
-5-(p-nitrobenzyl)-
-5-(o-trifluoroacetamidobenzyl)-
-5-(m-trifluoroacetamidobenzyl)-
-5-trifluoroacetamidobenzyl)-
-5-(o-trifluoromethylsulphonamidobenzyl)-
-5-(m-trifluoromethylsulphonamidobenzyl)-
-5-(p-trifluoromethylsulphonamidobenzyl)-
-5-(2-fluoro-6-nitrobenzyl)-
-5-(2-chloro-6-nitrobenzyl)-
-5-(2-furylmethyl)-
-5-(2-thienylmethyl)-
-5-(5-isoxazolylmethyl)-
-5-(5-methyl-3-isoxazolylmethyl)-
-5-(2-pyridylmethyl)-
-5-(3-pyridylmethyl)-
-5-(4-pyridylmethyl)-
-5-(2-furoylmethyl)-
-5-(2-thenoylmethyl)-
-5-(2-oxopropyl)-
-5-phenacyl-
-5-o-methoxyphenacyl-
-5-(2-oxobutyl)-
-5-(3-methyl-2-oxobutyl)-
-5-(3,3-dimethyl-2-oxobutyl)-
-5-o-nitrophenacyl-
-5-m-nitrophenacyl-
-5-p-nitrophenacyl-
-5-(3,3,3-trifluoro-2-oxopropyl)-
-5-(3,3,4,4,4-pentafluoro-2-oxobutyl)-
-5-nicotinoylmethyl-
-5-p-difluoromethoxyphenacyl-
-5-p-trifluoromethoxyphenacyl-
-5-p-cyanophenacyl-
-5-[2-(2-benzofuryl)-2-oxoethyl]-.

(b) The product (1 g) obtained as in (a) is dissolved in 60 ml of 4 N HCl in dioxane and stirred at 20° for 16 hours. The mixture is evaporated and worked up in the conventional manner and gives 2-cyclopropyl-4,5-dihydro-5-(o-ethoxycarbonylbenzyl)-4-oxo-3-[2'-(1H-5-tetrazolyl)biphenylyl -4-methyl]-3H-IP.

The 1H-5-tetrazolyl compounds given in Example 7b are obtained analogously from the corresponding 2-triphenylmethyl-2H -5-tetrazolyl compounds given in (a).

Example 9

Analogously to Example 7, 5-(2-benzoylethyl)-2-cyclopropyl-3-(p-2-cyano-2-phenylvinylbenzyl)-4,5-dihydro-4-oxo-3H-IP is obtained from 2-cyclopropyl-3-(p-2-cyano-2-phenylvinylbenzyl)-4,5-dihydro-4-oxo-3H-IP (obtainable from 2-cyclopropyl-4,5-dihydro-4-oxo-1 (or 3)H-IP and 3-p-bromomethylphenyl-2-phenylacrylonitrile) with 2-benzoyl-1-chloroethane.

Example 10

(a) Analogously to Example 7 (a), 2-cyclopentyl-3-(2'-cyanobiphenylyl-4-methyl)-4,5-dihydro-5-(o-methoxy-carbonylbenzyl)-4-oxo-3H-IP is obtained from 2-cyclopentyl-3-(2'-cyanobiphenylyl-4-methyl)-4,5-dihydro-4-oxo-3H-IP (obtainable by reaction of 3,4-diamino-2-chloropyridine with cyclopentanecarboxylic acid analogously to Example 3 to give 2-cyclopentyl-4,5-dihydro-4-oxo-1 (or 3) H-IP and reaction with 4'-bromomethyl-2-cyanobiphenyl)with methyl o-bromo methylbenzoate.

(b) Analogously to Example 7 (b), 2-cyclopentyl-4,5-dihydro-5-(o-methoxycarbonylbenzyl)-4-oxo-4-[2'-(1H-5-tetrazolyl)biphenylyl-4-methyl]-3H-IP is obtained therefrom with trimethyltin azide.

Example 11

A solution of 1 g of 2-cyclopropyl-4,5-dihydro-5-p-nitrophenacyl-4-oxo-3-[2'-(1H-5-tetrazolyl)biphenylyl -4-methyl]-3H-IP in 20 ml of methanol is hydrogenated on 0.3 g of 5% Pd-carbon at 20° and normal pressure until the calculated amount of $H_2$ has been absorbed. The catalyst is filtered off, and the filtrate is evaporated to give 5-p-aminophenacyl-2-cyclopropyl-4,5-dihydro-4-oxo-3-[2'-(1H-5-tetrazolyl)biphenylyl-4-methyl]-3H-IP.

The 2-cyclopropyl-4,5-dihydro-4-oxo-3-[2'-(1H-5-tetrazolyl) biphenylyl-4-methyl]-3H-IP below are obtained analogously by hydrogenation of the corresponding nitro compounds mentioned in Example 7b:

-5-o-aminophenacyl-
-5-m-aminophenacyl-.

Example 12

A solution of 2.82 g of trifluoromethanesulphonic anhydride in 10 ml of dichloromethane is added dropwise at −50° to −60° to a solution of 5.34 g of 5-p-amino-phenacyl-2-cyclopropyl-4,5-dihydro-4-oxo-3-[2'-(1H-5-tetrazolyl) biphenylyl-4-methyl]-3H-IP and 1.01 g of triethylamine in 30 ml of dichloromethane. The mixture is allowed to warm to 20°, is poured into dilute acetic acid and after conventional working-up gives 2 -cyclo-propyl-4,5-dihydro-4-oxo-3-[2'-(1H-5-tetrazolyl)biphenylyl-4-methyl]-5-p-trifluoromethanesulphonamidophenacyl-3H-IP.

The 2 -cyclopropyl-4,5-dihydro-4-oxo-3-[2'-(1H-5-tetrazolyl)biphenylyl-4-methyl]-3H-IP below are obtained analogously by acylation of the amino compounds mentioned in Example 11: pos
-5-o-trifluoromethanesulphonamidophenacyl-
-5-m-trifluoromethanesulphonamidophenacyl-.

The Examples below relate to pharmaceutical formulations containing active ingredients of the formula I or their salts.

Example A: Tablets and coated tablets

Tablets of the following composition are produced by compression in a conventional manner and, where required, are provided with a conventional sucrose-based coating:

| Active ingredient of the formula I | 100 mg |
|---|---|
| Microcrystalline cellulose | 278.8 mg |
| Lactose | 110 mg |
| Maize starch | 11 mg |
| Magnesium stearate | 5 mg |
| Finely divided silicon dioxide | 0.2 mg |

Example B: Hard gelatin capsules

Conventional two-part hard gelatin capsules are each filled with

| | |
|---|---|
| Active ingredient of the formula I | 100 mg |
| Lactose | 150 mg |
| Cellulose | 50 mg |
| Magnesium stearate | 6 mg |

Example C: Soft gelatin capsules

Conventional soft gelatin capsules are filled with a mixture of 50 mg of active ingredient and 250 mg of olive oil in each case, Example D: Ampoules A solution of 200 g of active ingredient in 2 kg of 1,2-propanediol is made up to 10 l with water and filled into ampoules so that each ampoule contains 20 mg of active ingredient.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. Imidazopyridine derivatives of the formula I:

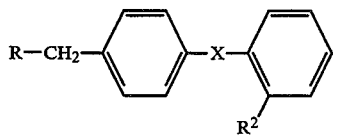

in which
R is

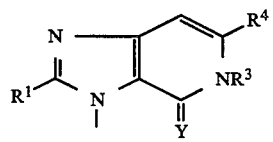

$R^1$ is $C_3$-$C_7$-cycloalkyl-$C_nH_{2n}$- or $C_1$-$C_6$-alkyl, in which a $CH_2$ group is replaced by O or S, $R^2$ is H, $COOR^6$, CN, $NO_2$, $NH_2$, $NHCOR^5$, $NHSO_2R^5$ or 1H-5-tetrazolyl, $R^3$ is —$C_mH_{2m}$—CN, $C_2$-$C_6$-alkynyl, —$C_mH_{2m}$—Ar, —$C_mH_{2m}$—CO-$R^5$, —$C_mH_{2m}$—CO—Ar, —$C_mH_{2m}$—Het or —$C_mH_{2m}$—CO—Het, $R^4$ is H or Hal, $R^5$ is $C_1$-$C_6$-alkyl, in which one or more H atoms can also be replaced by F, $R^6$ is H or A, X is a single bond or is —NH—CO—, —CO—NH—, —O—CH—(COOH)—, —NH—CH(COOH)—, —NA—CH(COOH), —CH=C—(COOH), —CH=C(CN) or —CH=C(1H-5-tetrazolyl)-, Y is O or S, A is alkyl having 1-6 C atoms, Ar is an unsubstituted phenyl group or a phenyl group which is monosubstituted or disubstituted by Hal, $R^5$, OH, $OR^5$, $COOR^6$, CN, $NO_2$, $NH_2$, NHA, $N(A)_2$, $NHCOR^5$, NHCOOA, $NHSO_2R^5$ and/or 1H-5-tetrazolyl, Het is a five- or six-membered heteroaromatic radical having 1 to 4N, O and/or S atoms, which can also be fused to a benzene or pyridine ring, Hal is F, Cl, Br or I, m is 1, 2, 3, 4, 5 or 6, and n is 0, 1, 2, 3, 4, 5 or 6, and their salts.

2. The imidazopyridine derivatives:
 a) 2-cyclopropyl-4,5-dihydro-5-(o-methoxycarbonylbenzyl)-4-oxo-3-[2'-(1H-5-tetrazolyl)biphenylyl-4-methyl]-3H-imidazo[4,5-c]-pyridine;
 b) 2-cyclopropyl-5-(o-ethoxycarbonylbenzyl)-4,5-dihydro-4-oxo-3-[2'-(1H-5-tetrazolyl)biphenylyl-4-methyl]-3H-imidazo[4,5-c]pyridine;
 c) 2-cyclopentyl-4,5-dihydro-5-(o-methoxycarbonylbenzyl)-4-oxo-3-[2'-(1H-5-tetrazolyl)biphenylyl-4-methyl]-3H-imidazo[4,5-c]pyridine; and
 d) 2-cyclopropyl-5-(o-chlorobenzyl)-4,5-dihydro-4-oxo-3-[2'-(1H-5-tetrazolyl)biphenylyl-4-methyl]-3H-imidazo[4,5-c]pyridine.

3. A pharmaceutical formulation which comprises at least one compound of the formula I according to claim 1, and/or one of its physiologically acceptable acid addition salts together with at least one solid, liquid or semi-liquid excipient or auxiliary.

4. A method for treating angiotensin(II)-dependent diseases or conditions, comprising administering an effective amount of a compound of the formula I and/or a physiologically acceptable acid addition salt thereof to a patient with such a disease or condition.

5. A method as in claim 4, wherein said disease is angiotensin(II)-dependent hypertension.

* * * * *